(12) United States Patent
Weeks

(10) Patent No.: US 6,518,318 B1
(45) Date of Patent: Feb. 11, 2003

(54) STIMULATING TRANSPORT OF GLUCOSE INTO ANIMAL TISSUE BY THE ADMINISTRATION OF PINITOL

(76) Inventor: Charles E. Weeks, 1235 Jensen Park Dr., New Albany, OH (US) 43054

(*) Notice: Subject to any disclaimer, the term of this patent is extended or adjusted under 35 U.S.C. 154(b) by 0 days.

(21) Appl. No.: 09/857,245

(22) PCT Filed: May 19, 2000

(86) PCT No.: PCT/US00/13872

§ 371 (c)(1),
(2), (4) Date: May 30, 2001

(87) PCT Pub. No.: WO00/71111

PCT Pub. Date: Nov. 30, 2000

Related U.S. Application Data

(60) Provisional application No. 60/135,008, filed on May 20, 1999.

(51) Int. Cl.$^7$ ............................................. A61K 31/075
(52) U.S. Cl. ........................................................ 514/714
(58) Field of Search .......................................... 514/714

(56) References Cited

U.S. PATENT DOCUMENTS

| | | | |
|---|---|---|---|
| 4,446,064 A | 5/1984 | Larner et al. | 260/112 R |
| 4,952,396 A | 8/1990 | Sabin et al. | 424/946 |
| 5,091,596 A | 2/1992 | Kennington et al. | 568/833 |
| 5,112,814 A | 5/1992 | Sabin | 514/75 |
| 5,122,603 A | 6/1992 | Larner et al. | 536/18.7 |
| 5,124,360 A | 6/1992 | Larner et al. | 514/738 |
| 5,183,764 A | 2/1993 | Kennington et al. | 436/131 |
| 5,283,260 A | 2/1994 | Miller et al. | 514/563 |
| 5,427,956 A | 6/1995 | Kennington et al. | 436/131 |
| 5,428,066 A | 6/1995 | Larner et al. | 514/738 |
| 5,516,950 A | 5/1996 | Piccariello et al. | 568/833 |
| 5,550,166 A * | 8/1996 | Ostlund et al. | 514/715 |
| 5,652,221 A | 7/1997 | Larner et al. | 514/35 |
| 5,827,896 A * | 10/1998 | Ostlund et al. | 514/715 |
| 5,834,473 A | 11/1998 | Virtanen et al. | 514/259 |
| 5,906,979 A | 5/1999 | Allan | 514/25 |
| 6,277,396 B1 | 8/2001 | Dente | 424/439 |
| 2001/0039297 A1 | 11/2001 | Allan | 514/763 |
| 2001/0056072 A1 | 12/2001 | Martin-Lomas et al. | 514/25 |
| 2002/0006904 A1 | 1/2002 | Gardiner et al. | 514/18 |

FOREIGN PATENT DOCUMENTS

| | | | |
|---|---|---|---|
| WO | WO 90/10439 | 9/1990 | A61K/31/045 |
| WO | WO 90/10711 | 9/1990 | C12Q/1/00 |
| WO | WO 91/12335 | 8/1991 | C12Q/1/00 |
| WO | WO 92/00744 | 1/1992 | A61K/31/66 |
| WO | WO 92/12706 | 8/1992 | A61K/31/045 |
| WO | WO 96/25381 | 8/1996 | C07C/35/16 |
| WO | WO 99/37309 | 7/1999 | A61K/31/70 |
| WO | WO 99/59564 | 11/1999 | A61K/31/045 |
| WO | WO 99/60406 | 11/1999 | G01N/33/66 |
| WO | WO 00/64454 | 11/2000 | A61K/33/32 |
| WO | WO 01/82921 | 11/2001 | A61K/31/047 |

OTHER PUBLICATIONS

Greenhaff et al., "The Nutritional Biochemistry of Creatine," *J. Nutr. Biochem.* vol. 8, No. 11, pp. 610–618, 1997, Abstract, Database CAPLUS on STN, No. 128:22136.

Handa, S.S. et al., "Hypoglycaemic plants –A review," *Fitoterapia*, vol. IX, No. 3, pp. 195–224, 1989.

Kennington, A.S. et al., "Low urinary chiro–inositol excretion in non–insulin–dependent disbetes mellitus, " *N. Engl. J. Med.*, vol. 323, No. 6, pp. 373–378, Aug. 9, 1990 (Abstract).

Klip, Amira et al., "Induction of sugar uptake response to insulin by serum depletion in fusing $L_6$ myoblasts," *American Journal of Physiology*, vol. 247, No. 3, pp. E291–E296, Sep. 1984.

Malaisse, Willy J. et al., "Determinants of the selective toxicity of alloxan to the pancreatic B cell," *Proc. Natl. Acad. Sci. USA*, vol. 79, pp. 927–930, Feb. 1982.

Musclelink's AnaVol–R Product Label, 2000.

Narayanan, C.R. et al., "Pinitol —a new anti–diabetic compound from the leaves of *Bougainvillea spectabilis*, " *Current Science*, vol. 56, No. 3, pp. 139–141, Feb. 5, 1987.

Nordin, Philip, "Preferential Leaching of Pinitol from Soybeans during Imbibition," *Plant Physiology*, vol. 76, No. 2, pp. 313–315, Oct. 1984.

Ostlund, Richard E. et al., "D–*chiro*–Inositol metabolism in diabetes mellitus," *Proc. Natl. Acad. Sci. USA*, vol. 90, pp. 1–6, 1993.

Pak, Yunbae et al., "In Vivo Conversion of [$^3$H]Myoinositol to [$^3$H]Chiroinositol in Rat Tissues," *The Journal of Biological Chemistry*, vol. 267, No. 24, pp. 16904–16910, Aug. 25, 1992.

Phillips, Daniel V. et al., "Cyclitols in Soybean," *Journal of Agriculture and Food Chemistry*, vol. 30, No. 3, pp. 456–458, Jan./Feb. 1982.

Plourde, Robert et al., "Synthesis and Characterization of an Insulin–Mimetic Disaccharide," *Journal of Organic Chemistry*, vol. 57, No. 9, pp. 2606–2610, 1992.

Protein Technologies International, *The Fiber of Choice...The Right Combination of Physiological and Functional Bebefits*, 1989.

Reaven, Gerald M., "Role of Insulin Resistance in Human Disease," *Diabetes*, vol. 37, pp. 1595–1606, Dec. 1988.

"Report of the Expert Committee on the Diagnosis and Classification of Diabetes Mellitus," *Diabetes Care*, vol. 23, Supplement I, pp. S4–S18, Jan. 2000.

(List continued on next page.)

Primary Examiner—Raymond Henley, III
(74) Attorney, Agent, or Firm—Michael S. Sherrill

(57) ABSTRACT

Enhanced muscle performance, including strength, recovery and endurance can be achieved by means of improved glucose transport and improved glycogen loading within animal muscle tissue through the administration of an effective amount of a pinitol compound. Pinitol alone, or in combination with a synergistic amount of insulin, is effective for controlling insulin-dependent diabetes.

14 Claims, No Drawings

OTHER PUBLICATIONS

Smith, A.E. et al., "Occurrence of Pinitol in Foliage of Several Forage Legume Species," *Crop Science*, vol. 20, pp. 75–77, Jan./Feb. 1980.

Suzuki, Susumu et al., "Urinary *chiro*–Inositol Excretion is an Index Marker of Insulin Sensitivity in Japanese Type II Diabetes," *Diabetes Care*, vol. 17, No. 12, pp. 1465–1468, Dec. 1994.

Yasu, Takeshi, "Dissimilarity in Low Molecular Weight Carbohydrate Composition of the Seeds of Cultivated Soybean [*Glycine max* (L.) MERRILL subsp. max]and Wild Soybean [G. max subsp. soja (SIEB ET ZUCC.) OHASHI]," *Agric. Biol. Chem.*, vol. 49, No. 4, pp. 933–937, 1985.

* cited by examiner

STIMULATING TRANSPORT OF GLUCOSE INTO ANIMAL TISSUE BY THE ADMINISTRATION OF PINITOL

This is a 371 of PCT/US00/13872 filed May 11, 2000, which claims priority to U.S. Provisional Application 60/135,008 filed May 20, 1999.

FIELD OF THE INVENTION

The invention relates to the use of pharmaceuticals and dietary supplements to stimulate the transport of glucose into animal tissue, particularly muscle tissue.

BACKGROUND

One of the factors involved in the performance of muscle tissue, especially during such physical activities as prolonged exercise routines and athletic events, is the ability of the muscle tissue to transport sufficient amounts of glucose into the tissue and convert the glucose into useable energy (i.e., ATP). While a wide variety of products and techniques have been developed in an attempt to accelerate the growth and development of muscle tissue (i.e., increasing muscle mass), little activity has focused upon improving the performance of existing muscle tissue.

SUMMARY OF THE INVENTION

I have discovered that glucose transport and glycogen loading within animal tissue can be stimulated and enhanced by administering an effective amount of a pinitol compound. Such stimulated glucose transport and enhanced glycogen loading is particularly effective for enhancing the performance of muscle tissue.

I have also discovered that pinitol alone, or in combination with a synergistic amount of insulin, is effective for controlling insulin-dependent diabetes.

In summary, I have discovered: (i) a method of enhancing performance of muscle tissue comprising administering an effective amount of a pinitol compound, preferably pinitol, to a human desiring such enhanced performance, (ii) a method of increasing glycogen loading in human tissue, including muscle tissue, comprising administering an effective amount of a pinitol compound, preferably pinitol, to a human desiring such increased glycogen loading, (iii) a method of stimulating transport of glucose into human tissue, including muscle tissue, comprising administering an effective amount of a pinitol compound, preferably pinitol, to a nondiabetic human desiring such stimulated transport of glucose, and (v) a method of controlling insulin-dependent diabetes comprising administering an effective amount of a pinitol compound, preferably pinitol, with or without the conjoint administration of an effective amount of insulin, to an insulin-dependent diabetic.

DETAILED DESCRIPTION OF THE INVENTION INCLUDING A BEST MODE

Definitions

As utilized herein, including the claims, the phrase "performance of muscle tissue" means contraction of the muscle tissue so as effect movement of the body (e.g., running, smiling or throwing a bowling ball) or exertion against a counteracting force (e.g., holding a bowling ball against the force of gravity).

As utilized herein, including the claims, the phrase "enhancing performance of muscle tissue" means (i) increasing the force with which the muscle tissue can contract (i.e., strength), (ii) decreasing the time required for the muscle tissue to recover after each contraction or series of contractions (i.e., recovery), and/or (iii) increasing the time period during which the muscle tissue can continuously or repetitively contract (i.e., endurance).

As utilized herein, including the claims, the term "pinitol compound" means pinitol, metabolites of pinitol, derivatives of pinitol and mixtures thereof.

As utilized herein, including the claims, the term "non-diabetic human" means a human who has NOT been diagnosed with non-insulin-dependent type II diabetes.

As utilized herein, including the claims, the term "insulin-dependent diabetic" means a human who has been diagnosed with insulin-dependent type I diabetes.

Active Ingredient

Pinitol is available from a number of natural sources (such as pine needles, chick peas and soy beans). Pinitol can also be synthetically produced. One procedure for extracting pinitol from soy beans is disclosed in U.S. Pat. No. 5,550,166, which is hereby incorporated by reference. A suitable grade of pinitol is also available from Humanetics Corporation under the mark Inzitol™.

Various derivatives and metabolites of pinitol are also effective for enhancing the performance of muscle tissue by increasing glycogen loading within the muscle tissue and stimulating the transportation of glucose into the muscle tissue. A nonexhaustive listing of suitable derivatives and metabolites include pinitol glycosides, pinitol phospholipids, esterified pinitol, lipid-bound pinitol, pinitol phosphates and pinitol phytates.

Administration

ADMINISTRATION ROUTE

The pinitol compound can be administered by virtually any of the commonly accepted practices for the administration of pharmaceutical preparations and dietary supplements including specifically, but not exclusively, mucosal administration, oral consumption, ocular administration, subcutaneous injection, transdermal administration, etc.

Mucosal administration of the active ingredients includes such routes as buccal, endotracheal, nasal, pharyngeal, rectal, sublingual, vaginal, etc. For administration through the buccal/sublingual/pharyngeal/endotracheal mucosa, the pinitol compound may be formulated as an emulsion, gum, lozenge, spray, tablet or an inclusion complex such as cyclodextrin inclusion complexes. Nasal administration is conveniently conducted through the use of a sniffing power or nasal spray. For rectal and vaginal administration, the ingredients may be formulated as a cream, douche, enema or suppository.

Oral consumption of the active ingredients may be effected by incorporating the ingredients into a food or drink, or formulating the ingredients into a chewable or swallowable tablet or capsule.

Ocular administration may be effected by incorporating the active ingredients into a solution or suspension adapted for ocular application such as drops or sprays.

Subcutaneous administration involves incorporating the active ingredients into a pharmaceutically acceptable and injectable carrier.

For transdermal administration, the active ingredients may be conveniently incorporated into a lipophilic carrier and formulated as a topical cream or adhesive patch.

DOSE RATE

The range of dosages and dose rates effective for achieving the desired biological response may be determined in accordance with standard industry practices. As a general guide, a dose rate of about 0.1 to 1,000 mg of pinitol compound per kg body weight per day, preferably about 1 to 100 mg of pinitol compound per kg body weight per day, should provide the desired biological response of enhancing the performance of muscle tissue by increasing glycogen loading within the muscle tissue and stimulating the transportation of glucose into the muscle tissue. Such a range of dosages and dose rates are also generally applicable when the pinitol is administered, with or without the conjoint administration of insulin, to control insulin-dependent type I diabetes.

Experimental

Testing Protocol

GLUCOSE UPTAKE

Glucose transport was tested and measured in accordance with the protocol set forth in Amira Kip et al., Induction of Sugar Uptake Response to Insulin by Serum Depletion in Fusing $L_6$ Myoblasts, American Journal of Physiology, Vol. 247, No. 3, Part 1 (September 1984), herein incorporated by reference, except that the cell culture was preincubated for only 2 hours and the cells treated with varying concentrations of pinitol, insulin or a combination thereof as set forth in Tables One through Three. The raw data, in terms of "counts per minute" as measured with a scintillation counter, is provided in Tables One and Two, while calculated data, in terms of "pmol min$^{-1}$ mg protein$^{-1}$," is provided in Table Three.

GLYCOGEN FORMATION

The method for glycogen incorporation is similar to that of J. Berger and N. S. Hayes, *Anal Biochem.* 261: 159–163 (1998), one of several standard references for radiolabeled (14-C) glucose incorporation into ethanol-precipitable glycogen. Into each well was added 1.25 mil of 1% TritonX100. The wells were then placed on a rotating agitator for 30 minutes to dissolve the cells. A 1 ml sample was removed from each well and placed in a 10 ml plastic tube. Into each sample was added 1 ml of a solution containing 18% trichloroacetic acid and 2 mg/ml of glycogen (added as carrier). The treated samples were placed on ice for 20 minutes and then centrifuged for 10 minutes at 10,000 RPM with the supernatant transferred to new plastic tubes. The remaining solids were washed by adding 0.3 ml of the trichloracetic acid-glycogen solution to the pellet, and centrifuged again as before. The combined supernatants were added to 4 ml of ice cold ethanol and 0.25 ml of 2% sodium sulphate (to help precipitate glycogen, as in L. Y. Hung and L. A. Menahan, *Biochemical Medicine*, Vol. 24: 356–360 (1980)). This was left overnight at 4° C. The precipitate was collected the next day by centrilugation at 10,000 RPM for 10 min. The precipitate was redisolved in water (2 ml) and reprecipitated as before with ethanol and sodium sulphate. The precipitate was dissolved in water, added to scintillation fluid, and radioactivity determined. Results are reported in Tables Four and Five.

Experiment One

GLUCOSE UPTAKE (Concentration)

TABLE 1

| ADDITIVE | CONCENTRATION (mM) | COUNTS PER MINUTE |
| --- | --- | --- |
| Control | NA | 5185 |
| Pinitol | 0.14 | 5221 |
| Pinitol | 1.44 | 6009 |

CONCLUSION: Pinitol alone does not meaningfully stimulate glucose transport at low concentrations (e.g., 0.14 mM), but can provide a significant stimulation in glucose transport at higher concentrations (e.g., 1.44 mM).

Experiment Two

GLUCOSE UPTAKE (Comparison of Pinitol, Insulin and Combination of Pinitol and Insulin)

TABLE 2

| ADDITIVE | CONCENTRATION (mM) | COUNTS PER MINUTE |
| --- | --- | --- |
| Control | NA | 3178 |
| Pinitol | 1.0 | 6007 |
| Insulin | $10^{-3}$ | 4477 |
| Pinitol + Insulin | $1.0/10^{-3}$ | 6332 |

TABLE 3

| ADDITIVE | CONCENTRATION (mM) | GLUCOSE TRANSPORT pmol · min$^{-1}$ · mg protein$^{-1}$ |
| --- | --- | --- |
| Control | NA | 151 |
| Pinitol | 0.14 | 155 |
| Insulin | $10^{-5}$ | 200 |
| Pinitol + Insulin | $0.14/10^{-5}$ | 241 |

CONCLUSION: Both pinitol and insulin, at higher concentrations, can provide a significant stimulation in glucose transport when administered alone, with the conjoint administration of pinitol and insulin, even at lower concentrations, providing a synergistic enhancement in glucose transport Experiment Three

GLYCOGEN FORMATION (Comparison of Pinitol, Insulin and Combination of Pinitol and Insulin)

TABLE 4

| ADDITIVE | CONCEN-TRATION mM | GLYCOGEN FORMATION nmol/min/mg | | | |
| --- | --- | --- | --- | --- | --- |
| | | 1$^{st}$ Set | 2$^{nd}$ Set | 3$^{rd}$ Set | Average |
| Control | — | 48.77 | 50.97 | 57.57 | 52.44 ± 4.58 |
| Pinitol | 1.4 | 68.36 | 79.08 | 64.37 | 70.60 ± 7.61 |
| Pinitol | 144.0 | 57.75 | 83.14 | 64.24 | 68.38 ± 13.19 |
| Insulin | $10^{-8}$ | 68.45 | 75.36 | — | 71.90 ± 4.89 |
| Insulin | $10^{-6}$ | 136.27 | 96.14 | 212.09 | 148.17 ± 58.89 |
| Pinitol + Insulin | $1.4/10^{-8}$ | 95.36 | 153.16 | 122.93 | 123.81 ± 28.91 |
| Pinitol + Insulin | $1.4/10^{-6}$ | 130.76 | 114.25 | 167.14 | 137.38 ± 27.06 |
| Pinitol + Insulin | $144/10^{-8}$ | 122.18 | 162.31 | 97.44 | 127.31 ± 32.74 |
| Pinitol + Insulin | $144/10^{-6}$ | 149.78 | 220.12 | 128.79 | 166.23 ± 47.83 |

TABLE FIVE

| | CONCENTRATION | GLYCOGEN FORMATION nmol/min/mg | | | | | | |
|---|---|---|---|---|---|---|---|---|
| ADDITIVE | Pintail (mM) Insulin (M) | 1st Set | 2nd Set | 3rd Set | 4th Set | 5th Set | 6th Set | Average |
| Control | — | 136.94 | 150.23 | 113.19 | 112.41 | 110.75 | 157.54 | 130.18 ± 20.87 |
| Pinitol | 1.4 | 102.40 | 117.18 | 183.05 | 113.15 | 124.64 | 158.40 | 133.14 ± 30.99 |
| Pinitol | 144 | 123.03 | 211.04 | 146.53 | 192.74 | 97.05 | 199.85 | 161.71 ± 46.39 |
| Insulin | $10^{-7}$ | 186.52 | 179.88 | 79.32 | 167.44 | 136.35 | — | 149.90 ± 43.91 |
| Pinitol + Insulin | $1.4/10^{-7}$ | 261.97 | 248.97 | 204.82 | 149.07 | 205.34 | — | 214.03 ± 44.44 |
| Pinitol + Insulin | $144/10^{-7}$ | 191.24 | 197.84 | 165.32 | 238.61 | 174.98 | 223.02 | 198.50 ± 27.99 |

CONCLUSION: Pinitol can provide a significant stimulation in glycogen formation when administered alone. The conjoint administration of pinitol with low levels of insulin (i.e., $10^{-7}$ M) provides a synergistic enhancement in glycogen formation.

I claim:

1. A method of enhancing performance of muscle tissue comprising administering an effective amount of a pinitol compound to a human desiring such enhanced performance.

2. The method of claim 1 wherein enhanced performance of muscle tissue is an increase in the strength of the muscle tissue.

3. The method of claim 1 wherein enhanced performance of muscle tissue is a decrease in recovery time of the muscle tissue.

4. The method of claim 1 wherein enhanced performance of muscle tissue is an increase in the endurance of the muscle tissue.

5. The method of claim 1 wherein the pinitol compound is pinitol.

6. A method of increasing glycogen loading in human tissue comprising administering an effective amount of a pinitol compound to a human desiring such increased glycogen loading.

7. The method of claim 6 wherein the pinitol compound is pinitol.

8. The method of claim 6 wherein the human tissue is muscle tissue.

9. A method of stimulating transport of glucose into human tissue comprising administering an effective amount of a pinitol compound to a nondiabetic human desiring such stimulated transport of glucose.

10. The method of claim 9 wherein the pinitol compound is pinitol.

11. The method of claim 9 wherein the human tissue is muscle tissue.

12. A method of controlling insulin-dependent diabetes comprising administering an effective amount of a pinitol compound to an insulin-dependent diabetic.

13. The method of claim 12 further comprising the conjoint administration of an effective amount of insulin to the insulin-dependent diabetic.

14. The method of claim 12 wherein the pinitol compound is pinitol.

* * * * *

UNITED STATES PATENT AND TRADEMARK OFFICE
CERTIFICATE OF CORRECTION

PATENT NO.    : 6,518,318 B1  Page 1 of 1
DATED         : February 11, 2003
INVENTOR(S)   : Weeks It is certified that error appears in the above-identified patent and that said Letters Patent is hereby corrected as shown below:

<u>Column 3,</u>
Line 32, replace "mil" with -- ml --
Line 48, replace "centrilugation" with -- centrifugation --

Signed and Sealed this

Twenty-second Day of July, 2003

JAMES E. ROGAN
*Director of the United States Patent and Trademark Office*